US008865459B2

(12) United States Patent
Narahara et al.

(10) Patent No.: US 8,865,459 B2
(45) Date of Patent: *Oct. 21, 2014

(54) NUCLEIC ACID ANALYSIS DEVICE AND NUCLEIC ACID ANALYZER USING THE SAME

(75) Inventors: Masatoshi Narahara, Hitachinaka (JP); Toshiro Saito, Hitachinaka (JP); Satoshi Takahashi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1249 days.

This patent is subject to a terminal disclaimer.

(21) Appl. No.: 12/173,472

(22) Filed: Jul. 15, 2008

(65) Prior Publication Data

US 2009/0023202 A1    Jan. 22, 2009

(30) Foreign Application Priority Data

Jul. 20, 2007    (JP) .................................. 2007-188989
Mar. 26, 2008   (JP) .................................. 2008-079494

(51) Int. Cl.
| | |
|---|---|
| B01L 3/00 | (2006.01) |
| G01N 21/00 | (2006.01) |
| G01N 21/64 | (2006.01) |
| G01N 21/05 | (2006.01) |

(52) U.S. Cl.
CPC ........ *G01N 21/648* (2013.01); *G01N 2021/058* (2013.01); *G01N 2021/6439* (2013.01); *G01N 21/6452* (2013.01); *G01N 21/6428* (2013.01); Y10S 435/808 (2013.01)
USPC ..................... 435/288.7; 435/808; 435/288.3; 435/287.9

(58) Field of Classification Search
CPC .......... G01N 21/6428; G01N 21/6452; G01N 21/648; G01N 2021/6439; G01N 2021/058; B10L 3/5027; B10L 2300/168
USPC .......................... 435/288.7, 808, 288.3, 287.9
See application file for complete search history.

(56) References Cited

U.S. PATENT DOCUMENTS

| | | | |
|---|---|---|---|
| 4,882,288 A | 11/1989 | North et al. | |
| 7,033,764 B2 * | 4/2006 | Korlach et al. | ............... 435/6.12 |

(Continued)

FOREIGN PATENT DOCUMENTS

| | | |
|---|---|---|
| EP | 0 965 835 A2 | 12/1999 |
| EP | 1 445 601 A | 8/2004 |

(Continued)

OTHER PUBLICATIONS

European Search Report issued in European Patent Application No. EP 08012794.7-2204 dated Feb. 9, 2009.

(Continued)

*Primary Examiner* — Nathan Bowers
(74) *Attorney, Agent, or Firm* — McDermott Will & Emery LLP

(57) ABSTRACT

The present invention relates to a nucleic acid analysis device for analysis of nucleic acid in a sample through fluorometry, in which a localized surface plasmon by light irradiation, and in which a nucleic acid probe or a nucleic acid synthase for the analysis of the nucleic acid in the sample is disposed in a region of generation of the surface plasmon. The present invention allows the fluorescence intensifying effect of the surface plasmon to be produced efficiently and also enables the immobilization of a DNA probe or the nucleic acid synthase in a region on which the fluorescence intensifying effect is exerted, thus making it possible to carry out a measurement on the base elongation reaction without having to remove the unreacted substrate with the fluorescent molecule.

7 Claims, 6 Drawing Sheets

(56) References Cited

U.S. PATENT DOCUMENTS

| | | | |
|---|---|---|---|
| 7,898,659 B2* | 3/2011 | Naya | 356/318 |
| 2002/0123132 A1 | 9/2002 | Tanaami et al. | |
| 2004/0029152 A1 | 2/2004 | Ishida | |
| 2005/0045977 A1* | 3/2005 | Lin et al. | 257/428 |
| 2005/0064432 A1* | 3/2005 | Huang et al. | 435/6 |
| 2005/0079635 A1* | 4/2005 | Norman | 436/514 |
| 2005/0105085 A1* | 5/2005 | Naya | 356/301 |
| 2005/0202504 A1* | 9/2005 | Anderson et al. | 435/6 |
| 2006/0192115 A1 | 8/2006 | Thomas et al. | |
| 2006/0228735 A1* | 10/2006 | Bobrow et al. | 435/6 |
| 2007/0111366 A1 | 5/2007 | Odom et al. | |
| 2007/0158549 A1 | 7/2007 | Naya et al. | |
| 2008/0105831 A1* | 5/2008 | Reel et al. | 250/458.1 |
| 2009/0128822 A1* | 5/2009 | Yamamichi et al. | 356/445 |
| 2009/0140128 A1* | 6/2009 | Oldham et al. | 250/216 |

FOREIGN PATENT DOCUMENTS

| | | |
|---|---|---|
| EP | 1 553 400 A | 7/2005 |
| JP | 10-267841 | 10/1998 |
| JP | 2001-194310 A | 7/2000 |
| JP | 2002-214142 A | 7/2002 |
| JP | 2005-308658 | 11/2005 |
| JP | 2005-337771 A | 12/2005 |
| JP | 2007-240361 A | 9/2007 |
| WO | WO 2004/068141 A1 | 8/2004 |
| WO | WO 2007/015556 A1 | 2/2007 |

OTHER PUBLICATIONS

Braslavsky, Ido et al., "Sequence information can be obtained from single DNA molecules," PNAS vol. 100, No. 7. Apr. 1, 2003, p. 3960-3964.

Anger, Pascal et al., "Enhancement and Quenching of Single-Molecule Fluorescence," Physical Review Letters 96, 113002, Mar. 24, 2006.

Fu, Yi, et al., "Enhanced Fluorescence of Cy5-Labeled DNA Tethered to Silver Island Films: Fluorescence Images and Time-Resolved Studies Using Single-Molecule Spectroscopy," Analytical Chemistry, vol. 78, No. 17, Sep. 1, 2006.

Bharadwaj, Palash et al., "Nanoplasmonic enhancement of single-molecule fluorescence," Institute of Physics Publishing Ltd., Nanotechnology 18, 040017, 2007, pp. 1-5.

Kappeler, Roman et al., "Field Computations of Optical Antennas," Journal of Computational and Theoretical Nanoscience, vol. 4, No. 3, 686-691, 2007.

Esteban, R. et al., "Simulation of optical near and far fields of dielectric apertureless scanning probes," Institute of Physics Publishing, Nanotechnoolgy 17, 2006, pp. 475-482.

Ju, Jingyue, et al., :Four-color DNA sequencing by synthesis using cleavable fluorescent nucleotide reversible terminators, PNAS, vol. 103, No. 52, pp. 19635-19640, Dec. 26, 2006.

Toyama et al "Design and Fabrication of a waveguide-coupled prism device for surface Plasmon resonance sensor" pp. 32-34 Sensors and Actuators B 65 Elsevier Science S. A. 2000 www.Elsevier.nl/locate/senssorb.

GIAKOS "Exploitation of Enhanced Florescence via Cross-Coupling of Principles Toward the Design of an Optical Integrated Thin Film Sensor for Nanotechnology and Biomedical Application" pp. 970-975 IEEE Transations on Instrumentation and Measurement vol. 51, No. 5 IEEE Oct. 2002.

Partial European Search Report Issued in European Patent Application No. EP 08012794.7-2204 dated on Nov. 10, 2008.

Japanese Office Action issued in Application No. 2008-079494 issued on Mar. 27, 2012.

* cited by examiner

NUCLEIC ACID ANALYSIS DEVICE AND NUCLEIC ACID ANALYZER USING THE SAME

BACKGROUND OF THE INVENTION

1. Field of the Invention

The present invention relates to a nucleic acid analysis device and a nucleic acid analyzer using the same.

2. Description of the Related Art

There is a new development in a technique as a nucleic acid analysis device for determining DNA (deoxyribonucleic acid) or RNA (ribonucleic acid) sequences.

A method utilizing electrophoresis, which is now in general use, involves preparing beforehand a cDNA (complementary DNA) fragment sample synthesized through a reverse transcription reaction of a DNA fragment or an RNA sample for sequence determination; executing a dideoxy chain termination reaction by well-known Sanger's sequencing method; thereafter performing electrophoresis for the sample; and making a measurement on a pattern of separation and development of molecular weight to analyze the pattern.

In contrast to this, there has recently been proposed a method in which immobilization of DNA or the like on a substrate takes place for DNA sequence determination, as disclosed in P.N.A.S. 2003, Vol. 100, pp. 3960-3964. The method involves trapping fragments of sample DNA to be analyzed, molecule by molecule, on the surface of the substrate in a random manner; elongating the sample DNA on substantially a base-by-base basis; and detecting the result through fluorometry, thereby effecting the sequence determination. Specifically, the nucleotide sequence determination for the sample DNA is accomplished by repeating a cycle including: a step of effecting the occurrence of a DNA polymerase chain reaction, using four types of derivatives (MdNTP) of dNTP (deoxyribonucleotide triphosphate) as a substrate of DNA polymerase, in which the MdNTP can be captured in template DNA to stop its DNA chain elongation reaction by the presence of a protecting group and moreover in which the MdNTP has a detectable label; subsequently a step of detecting the captured MdNTP by its fluorescence or the like; and a step of restoring the MdNTP to its elongation-capable state. Since this technique makes it possible to determine the sequence for the DNA fragments molecule by molecule, many fragments can be analyzed at a time, and hence an increase in analysis throughput is achieved. Also, this method can possibly be capable of the nucleotide sequence determination for each of single DNA molecules and thus be capable of eliminating the need for purification or amplification of the sample DNA, using cloning, PCR (polymerase chain reaction), or the like. Since the purification or amplification has been a problem involved in the prior art, the method can be expected to achieve a speedup in genome analysis or gene diagnosis.

SUMMARY OF THE INVENTION

For nucleotide sequence analysis using an elongation reaction on a substrate, what is called a consecutive reaction method is generally used as represented by the above method disclosed in P.N.A.S. 2003, Vol. 100, pp. 3960-3964. The method has a cycle including a one-base elongation reaction and cleaning and measurement of an unreacted substrate. For the nucleotide sequence analysis for each of single DNA molecules, a measurement is made on fluorescence of one molecule of fluorescent dye attached on the probe DNA to nucleotide captured in double-stranded DNA due to the one-base elongation reaction. However, typical fluorometry is incapable of distinguishing between a fluorescent molecule trapped on the probe DNA and the fluorescent dye attached to unreacted nucleotide and suspended in the vicinity of the fluorescent molecule. It is therefore essential that the unreacted substrate be cleaned after each one-base elongation. The interposition of this cleaning process leads to problems of: a need to form on the substrate a complicated fluid channel or a solution feeding device and a waste fluid disposal device; heavy consumption of a reaction reagent; and to the problem of increasing the length of reaction time required for the overall analysis.

In order to distinguish between one molecule of the fluorescent dye trapped on the probe DNA and the fluorescent molecule of the unreacted substrate, conditions must be established such that only the fluorescent dye trapped on the probe DNA emits light intensely, while the suspended dye does not emit light or emits negligibly weak light.

An object of the present invention relates to distinguishing between one molecule of the fluorescent dye attached to the nucleotide captured in the double-stranded DNA due to the base elongation reaction and the fluorescent molecule of the unreacted substrate.

As a result of having devoted their efforts to study, therefore, the inventors have found out a method in which a strong fluorescence intensifying field based on a localized surface plasmon is formed on the probe DNA or a nucleic acid synthase to thereby enable measurement capable of distinguishing between the fluorescent dye attached to the nucleotide captured in the double-stranded DNA due to the base elongation reaction and the suspended dye. More particularly, by devoting their efforts to a study of the shape of a metal structure for producing the strong fluorescence intensifying field and a method for immobilization of the probe DNA or the nucleic acid synthase in the localized intensifying field, the inventors have found out a method capable of achieving both of them.

The present invention relates to a nucleic acid analysis device for analysis of nucleic acid in a sample through fluorometry, in which a localized surface plasmon is generated by light irradiation, and in which a nucleic acid probe or a nucleic acid synthase for the analysis of the nucleic acid in the sample is disposed in a region of generation of the surface plasmon.

The present invention allows the fluorescence intensifying effect of the surface plasmon to be produced efficiently and also enables the immobilization of the DNA probe or the nucleic acid synthase in the region on which the fluorescence intensifying effect is exerted, thus making it possible to carry out a measurement on the base elongation reaction without having to remove the unreacted substrate with the fluorescent molecule.

DETAILED DESCRIPTION OF THE PREFERRED EMBODIMENTS

Figure 1:
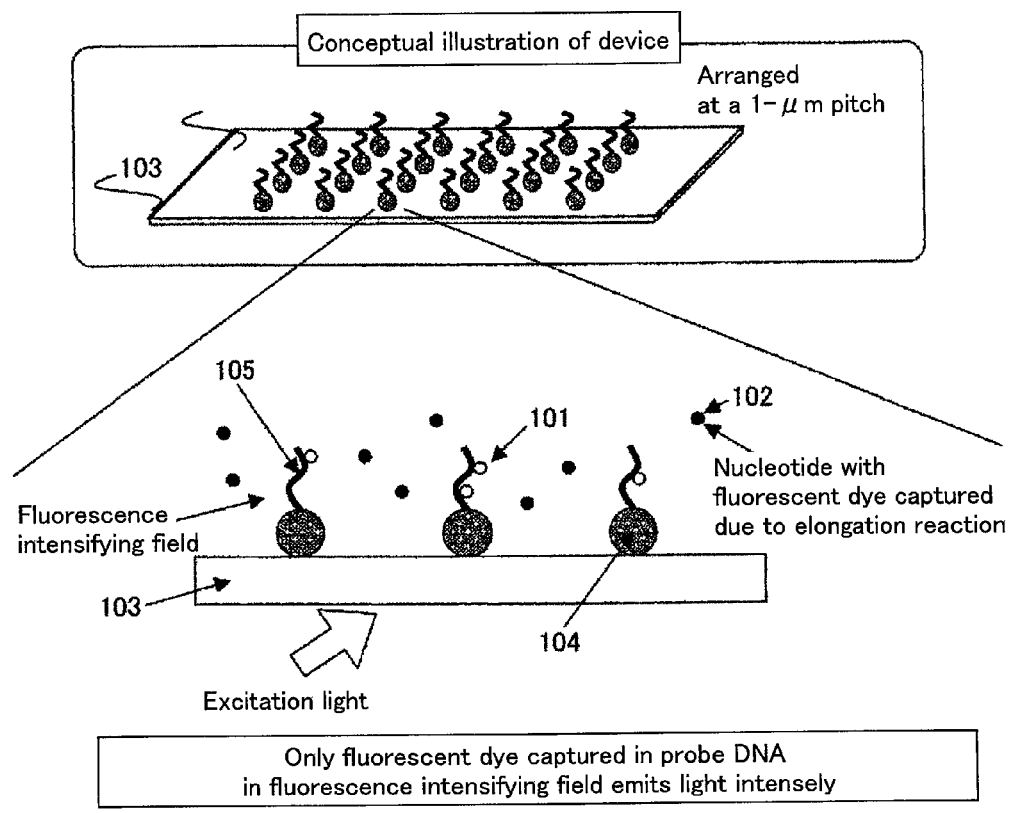
FIG. 1 is an illustration for explaining the concept of a nucleic acid analysis device of the present invention.

An embodiment of the present invention is a nucleic acid analysis device for analysis of nucleic acid in a sample through fluorometry, characterized by including a metal structure in which a localized surface plasmon is generated by light irradiation, and a nucleic acid probe for the analysis of the nucleic acid in the sample is disposed in a region of generation of the surface plasmon.

Also, an embodiment of the present invention is a nucleic acid analysis device for analysis of nucleic acid in a sample through fluorometry, characterized in that a metallic material, an insulating layer, and a metallic material are deposited in listed order on a flat supporting substrate in a direction perpendicular to the surface of the supporting substrate, and the insulating layer has a nucleic acid probe for the analysis of the nucleic acid in the sample.

Further, an embodiment of the present invention is a nucleic acid analysis device for analysis of nucleic acid in a sample through fluorometry, characterized in that a metal structure of a shape having a vertex and a thin film layer made of a material other than the metal are provided on a flat supporting substrate, a part of the metal structure including the vertex is exposed from the thin film layer, the metal structure, except for the part, is buried in the thin film layer, and a nucleic acid probe for the analysis of the nucleic acid in the sample is provided on the exposed surface of the metal structure.

Further, an embodiment of the present invention is a nucleic acid analysis device for analysis of nucleic acid in a sample through fluorometry, characterized in that a metal structure of a shape having a vertex and a thin film layer made of a material other than the metal are provided on a flat supporting substrate, a part of the metal structure including the vertex is exposed from the thin film layer, and the metal structure, except for the part, is buried in the thin film layer, and in that the fabrication of the nucleic acid analysis device is accomplished by immobilizing a nucleic acid probe for the analysis of the nucleic acid in the sample on the exposed surface of the metal structure, and thereafter removing the thin film layer.

Further, an embodiment of the present invention is a nucleic acid analysis device for analysis of nucleic acid in a sample through fluorometry, including a metal structure in which a localized surface plasmon is generated by light irradiation, wherein a nucleic acid synthase for the analysis of the nucleic acid in the sample is disposed in a region on which the localized surface plasmon is generated.

Further, an embodiment of the present invention is a nucleic acid analysis device for analysis of nucleic acid in a sample through fluorometry, including a flat supporting substrate, wherein a metallic material, an insulating layer, and a metallic material are deposited in listed order on the supporting substrate in a direction perpendicular to the surface of the supporting substrate, and the insulating layer has a nucleic acid synthase for the analysis of the nucleic acid in the sample.

Further, an embodiment of the present invention is a nucleic acid analysis device for analysis of nucleic acid in a sample through fluorometry, including a flat supporting substrate, wherein a metal structure of a shape having a vertex and a thin film layer made of a material other than the metal are provided on the supporting substrate, a part of the metal structure is exposed from the thin film layer, and a nucleic acid synthase for the analysis of the nucleic acid in the sample is provided on the exposed surface of the metal structure.

Further, an embodiment of the present invention is the nucleic acid analysis device set forth above, characterized in that the structure has a conical shape.

Further, an embodiment of the present invention is the nucleic acid analysis device set forth above, characterized in that the structure is a polyhedron.

Further, an embodiment of the present invention is the nucleic acid analysis device set forth above, characterized in that a noble metal selected from a group consisting of gold, silver and platinum is used as the metal.

Further, an embodiment of the present invention is the nucleic acid analysis device set forth above, characterized in that the metal structures are arranged in an array on the supporting substrate.

Further, an embodiment of the present invention is a nucleic acid analyzer, characterized by including a means for irradiating a sample with light; and a luminescence detecting means, and characterized in that a nucleic acid sample undergoes hybridization on the nucleic acid analysis device set forth above and that nucleotide having fluorescent dye and a nucleic acid synthase coexist together on the device so that a nucleic acid elongation reaction occurs on the device, and then a measurement is made on fluorescence of the fluorescent dye captured in a nucleic acid chain during the elongation reaction, whereby nucleotide sequence information on the nucleic acid sample is obtained.

Further, an embodiment of the present invention is a nucleic acid analyzer, characterized by including a means for supplying nucleotide having fluorescent dye, a primer and a nucleic acid sample to the nucleic acid analysis device; a means for irradiating the nucleic acid analysis device with light; and a luminescence detecting means for making a measurement on fluorescence of the fluorescent dye captured in a nucleic acid chain due to a nucleic acid elongation reaction induced by the coexistence of the nucleotide, the primer and the nucleic acid sample on the nucleic acid analysis device, wherein nucleotide sequence information on the nucleic acid sample is obtained.

Description will be given below with reference to the drawings with regard to the above and other novel features and effects of the present invention.

Although detailed description is given herein with regard to specific embodiments for complete understanding of the present invention, it is to be understood that the present invention is not limited to the disclosure given herein.

First Embodiment

The concept of the device according to the first embodiment will be described with reference to FIG. 1. In order to distinguish between fluorescent dye 101 trapped on the probe DNA and a fluorescent molecule 102 of an unreacted substrate, it is required that the intensity of light for irradiating the fluorescent dye 101 trapped on the probe DNA be different from the intensity of light for irradiating the suspended unreacted fluorescent dye 102, or that a radiation process of only the dye 101 on the probe DNA occur efficiently. The first embodiment is based on the concept of the latter, and is based on a physical phenomenon in which a localized surface plasmon increases the probability of both an electronic transition of the molecules caused by optical absorption and a radiation transition from an excitation singlet to a base state, as reported in Physical Review Letters 2006, 96, pp 113002-

113005. The fluorescence intensifying effect of the localized surface plasmon can be expected to increase the intensity of fluorescence by approximately several times to several tens of times. The influence of the effect is exerted within a range of about 10 nm to 20 nm, and thus, when the localized surface plasmon is generated on the surface of a metal structure having the probe DNA immobilized thereon, only the dye captured in the probe DNA benefits from fluorescence intensification, so that a difference in fluorescence intensity arises between the captured dye and the suspended dye. The fluorescence intensity of the captured dye is several times to several tens of times or more times that of the suspended dye. A region in which the localized surface plasmon is generated and the range upon which the influence is exerted lie between about 10 and 20 nm. Therefore, the immobilization of the probe DNA in such a region is extremely difficult, and, as far as the inventors know, there has hitherto been no report on an instance of fabrication, on a flat substrate, of the regions on the order of tens of thousands to hundreds of thousands in which the localized surface plasmon is generated as mentioned above. The first embodiment is intended to find out a method for simple and easy immobilization of the probe DNA in the region in which the localized surface plasmon is generated, and is also intended to provide a method capable of the fabrication, on a flat substrate 103, of the regions on the order of tens of thousands to hundreds of thousands in which the localized surface plasmon is generated as mentioned above.

Concerning the phenomenon of fluorescence intensification by the surface plasmon, there are known the use of an islands structure of silver of the order of nanometers as reported in Anal. Chem. vol. 78, 6238-6245, and the use of a spherical fine particle of gold having a diameter of several tens of nanometers as reported in Nanotechnology, 2007, vol. 18, pp 044017-044021.

Pads having the islands structure or spherical fine particles on the order of several tens of thousands to several hundreds of thousands can be hardly disposed on the flat substrate such as a glass substrate for each individual molecule of the probe DNA. Particularly, it is impossible to immobilize the molecules of the probe DNA in predetermined locations.

Therefore, the inventors have devoted their efforts to a study of a structure capable of production of a strong surface plasmon and also immobilization of the molecules of the probe DNA in the vicinity of the region of generation of the surface plasmon. Further, the inventors have studied the structure, considering preferable the structure capable of being fabricated by utilizing a thin film process for use in semiconductor or wiring board fabrication in consideration for manufacturing costs.

A computer simulation has predicted that, if fine nano-particles of gold are in close proximity to each other, a strong localized surface plasmon is generated in a gap between the fine particles, as described in J. Comput. Theor. Nanosci. 2007, vol. 4, pp 686-691. However, it is very difficult to bring fine nano-particles of gold into close proximity with each other and thereby form pairs of fine particles, arrange the pairs of fine nano-particles of gold in a lattice on the flat substrate while controlling the distance between the fine particles, and immobilize a DNA probe between the fine particles of gold that form each pair. As a result of having devoted their efforts to study, the inventors have contrived a structure in which an insulating layer is sandwiched in between the metal structures, the distance between the metal structures is controlled by controlling the thickness of the insulating layer, and the molecules of the probe DNA are immobilized on the insulating layer.

An inorganic material such as $SiO_2$ (silicon oxide) or an organic material represented by polyimide can be used for the insulating layer to be interposed between the metal structures. In any of these instances, the fabrication of the metal structure with a desired probe DNA molecule can be accomplished, using a difference in chemical properties between the surface of the insulating layer and the surface of the metal, by selecting an appropriate functional group, either imparting the functional group to the insulating layer or premodifying the end of the molecule of the probe DNA with the functional group, and allowing the functional group to react with the metal structure. Preferably, the layer thickness of the insulating layer lies between about 1 nm and 20 nm; however, it is to be understood that the layer thickness is not restricted to this condition. The fabrication of the metal structure can be accomplished by forming a thin film by means of vapor deposition and sputtering either with or without the use of a mask, and then subjecting the thin film to either dry etching or wet etching. The fabrication of the metal structure of a desired shape may be accomplished by forming a film by depositing a metal, an insulator, and a metal in sequence by means of vapor deposition and sputtering, and then subjecting the film to etching or the like, or may be accomplished by depositing a metal, an insulator, and a metal one on top of another by means of vapor deposition and sputtering through a mask. Alternatively, the fabrication of a desired metal laminated structure may be accomplished by bonding a metal foil to insulators with the metal foil sandwiched in between the insulators, then bonding the laminated structure to the flat substrate, and shaping the laminated structure by means of etching or the like. The appropriate size of the metal structure varies according to the wavelength of light for irradiation. In other words, a resonance frequency suitable for surface plasmon generation depends on the interaction between a group of free electrons and light on the surface of the metal structure. If visible light is used as excitation light, it is appropriate that the dimensions of the metal structure are such that both the width and height thereof lie between about 30 nm and 1000 nm; however, it is to be understood that the dimensions are not restricted to this condition. For use as the metal, a metal having a negative dielectric constant of greater magnitude is preferable, or a noble metal such as gold, silver or platinum is desirable, because the formation of a greater opposite polarization field (or equivalently, an electric field having the opposite phase to an applied electric field produced by light) in the metal by the electric field produced by the light leads to the formation of the strong localized surface plasmon.

A micro-needle having a sharp tip is known as another structure in which the strong surface plasmon is generated. As disclosed for example in Nanotechnology, 2006, vol. 17, pp 475-482, the probability that sharper tip yields a stronger surface plasmon is predicted by calculation simulation. However, it is very difficult to arrange metal needles with sharp tips in a lattice pattern on the flat substrate and immobilize DNA probes on the tips. As the result of intensive study, the inventors have contrived a metal structure with a probe DNA molecule immobilized only on the metal tip. The immobilization is achieved by coating the metal structure with a different metal from the above-mentioned metal so that only the tip is exposed, and by utilizing the difference in adhesion to molecules of the probe DNA between the above-mentioned metal and a material. Preferably, the metal structure having the sharp tip is of a conical shape or a polyhedron having many angles; however, the shape of the metal structure is not limited to this condition. An inorganic material such as $SiO_2$ or an organic material such as a macromolecule is suitable for the material that coats the above-mentioned structure. Fabrication of the metal structure can be accomplished by depositing a metal by vapor deposition and sputtering through a mask having a large taper. After the fabrication of the metal structure, a thin film of an inorganic material such as $SiO_2$ or an organic material such as a macromolecule is formed throughout the entire surface of the metal structure. Vapor deposition and sputtering, or liquid application is suitable for a formation method for the thin film. The tip can be exposed by controlling the thickness of the film. Alternatively, the exposure of the tip may be accomplished by forming the thin film so thickly that the tip is coated, and performing etching for the thin film. The difference in chemical properties between the surface of the metal structure and the surface of the thin film can be utilized for immobilization of the molecules of the probe DNA on the exposed portion. For example, if the metal is gold and the film that coats the metal is made of $SiO_2$, the end of the probe DNA is premodified with a thiol group, and an aqueous solution of the probe DNA is applied after the formation of the $SiO_2$ coated film, and thereby, the probe DNA is immobilized only on the metal exposed portion. An appropriate size of the metal structure varies according to the wavelength of light for irradiation. Specifically, a resonance frequency suitable for generation of the surface plasmon is determined by the interaction between a free electron group on the surface of the metal structure and the light. If excitation light is visible light, dimensions of about 30 nm to 1000 nm are suitable for both the width and height of the metal structure; however, the size of the metal structure is not limited to this condition. Also, the effect of the surface plasmon is equivalent even if the thin film that coats the metal structure is removed after the immobilization of the probe DNA on the tip by the above method. Preferably, the thin film that coats the metal structure is removed if the thin film adversely affects the properties of the nucleic acid analysis device.

Figure 2:
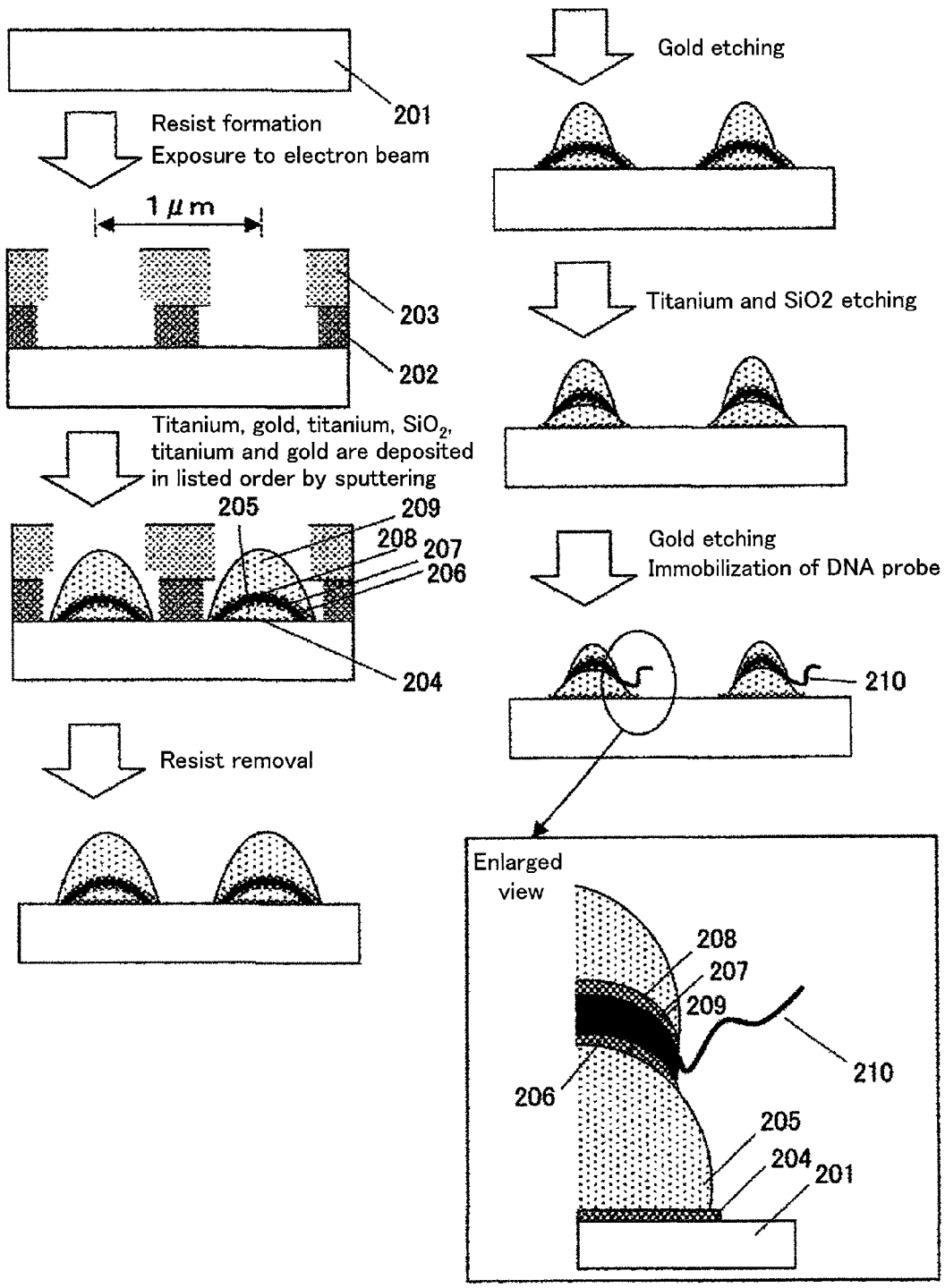
FIG. 2 is a view for explaining an example of a fabrication method for the nucleic acid analysis device of the present invention.

Description will be given with reference to FIG. 2 with regard to a fabrication method for the nucleic acid analysis device having the DNA probe immobilized between two metal structures in proximity to each other. A flat supporting substrate 201 is coated separately with two types of electron beam positive resists 202 and 203 by a spin coating method. A glass substrate, a sapphire substrate, a resin substrate, or the like is used as the flat supporting substrate. For the device, a quartz substrate or a sapphire substrate having excellent light transmittance can be used if it is necessary to irradiate the device with excitation light from the rear surface opposed to the surface on which the metal structure is formed. A combination of polymethyl methacrylate and a macromolecular resist having a structure capable of easy depolymerization by radical cutting, for example, can be used as the two types of electron beam positive resists. For the latter resist, it is preferable that the resist be capable of undergoing prebaking by a hot plate at 1700 to 200° for about 2 to 5 minutes and also capable of undergoing electron beam writing at an electron dose of 20° C./cm² to 50 µC/cm² at an accelerating voltage of 20 KV as a matter of practicality, and for example, the resists include ZEP-520A (available from Zeon Corporation). Alignment takes place using the position of a marker on the substrate and then, a direct electron beam exposure takes place twice, and thereby, a through hole is formed in each of the resists so that a hole diameter of the resist 202 closer to the substrate is larger than that of the resist 203. For example, the through holes having a diameter of 300 nm and a diameter of 250 nm, respectively, are formed. The through holes are used for a mask for deposition having a large taper. The through holes depend on molecularity of nucleic acid that can be analyzed by parallel processing, and a pitch of about 1 µm is suitable, allowing for ease and simplicity of fabrication, yield, and the molecularity of nucleic acid that can be analyzed by parallel processing. A region where the through holes are formed depends on the molecularity of nucleic acid that can be analyzed by parallel processing, and also depends greatly on the position accuracy of the detector and the position resolution thereof. For example, if a reaction site (namely, the metal structure) is configured at a pitch of 1 µm, one million reaction sites can be formed, provided that the region where the through holes are formed is 1 mm×1 mm. After the formation of the through holes, titanium 204, gold 205, titanium 206, a $SiO_2$ film 207, titanium 208, and gold 209 are deposited by sputtering according to the composition of the metal structure. Preferably, the titanium is used in order to reinforce a bond between the sapphire and the gold and a bond between the gold and $SiO_2$, or other metal such as chromium may be used. After the removal of the two-layer resist, the gold 209 is subjected to etching so that the titanium 208 is exposed. Preferably, wet etching is used for the etching of the gold 209, and preferably, an iodine-base etchant is used as an etchant therefor. The iodine-base etchant is formed of iodine and iodide (e.g., potassium iodide or ammonium iodide), and has the advantage of being easy to treat because of being neutral and also has the advantage of facilitating control of an etching rate by component density. As an example, the etchants include AURUM-301 (available from Kanto Chemical Co., Inc.). Then, the titanium 208, the $SiO_2$ film 207 and the titanium 206 are subjected to dry etching so that the lower gold 205 is exposed. For this etching, it is preferable that argon plasma etching be used. Then, the gold is again subjected to wet etching so that the width of the gold 205 lies between about 100 nm and 500 nm. It is required that the final size of the gold 205 be adjusted by the wavelength of light for irradiation for generation of the localized surface plasmon. For example, if light of about 500 nm is used, it is effective that the width lies between about 50 nm and 500 nm and the height lies between about 50 nm and 500 nm. Finally, the DNA probe is immobilized on the $SiO_2$ film 207. Although various methods for immobilization can possibly be used, a method using an aminosilane process will be described as an example. In the aminosilane process, an amino group is introduced into the $SiO_2$ film 207. After that, biotin-succinimide (e.g., NHS-Biotin available from Pierce Corporation) is allowed to undergo a reaction, thereafter streptoavidin is allowed to undergo a reaction, and then a DNA probe 210 whose end is premodified with biotin is allowed to undergo a reaction, and thereby the nucleic acid analysis device having the DNA probe immobilized between the two metal structures in proximity to each other can be brought into completion. The length of the DNA probe is not particularly limited; however, an excessively long or short length of the DNA probe can possibly lead to the hiding of DNA behind the metal structures, resulting in impairment of the efficiency of hybridization with a nucleic acid sample. Preferably, the number of bases lies between 20 and 50. It goes without saying that the above fabrication method may be used in the same manner even if silver or platinum, besides gold, is used.

Figure 3:
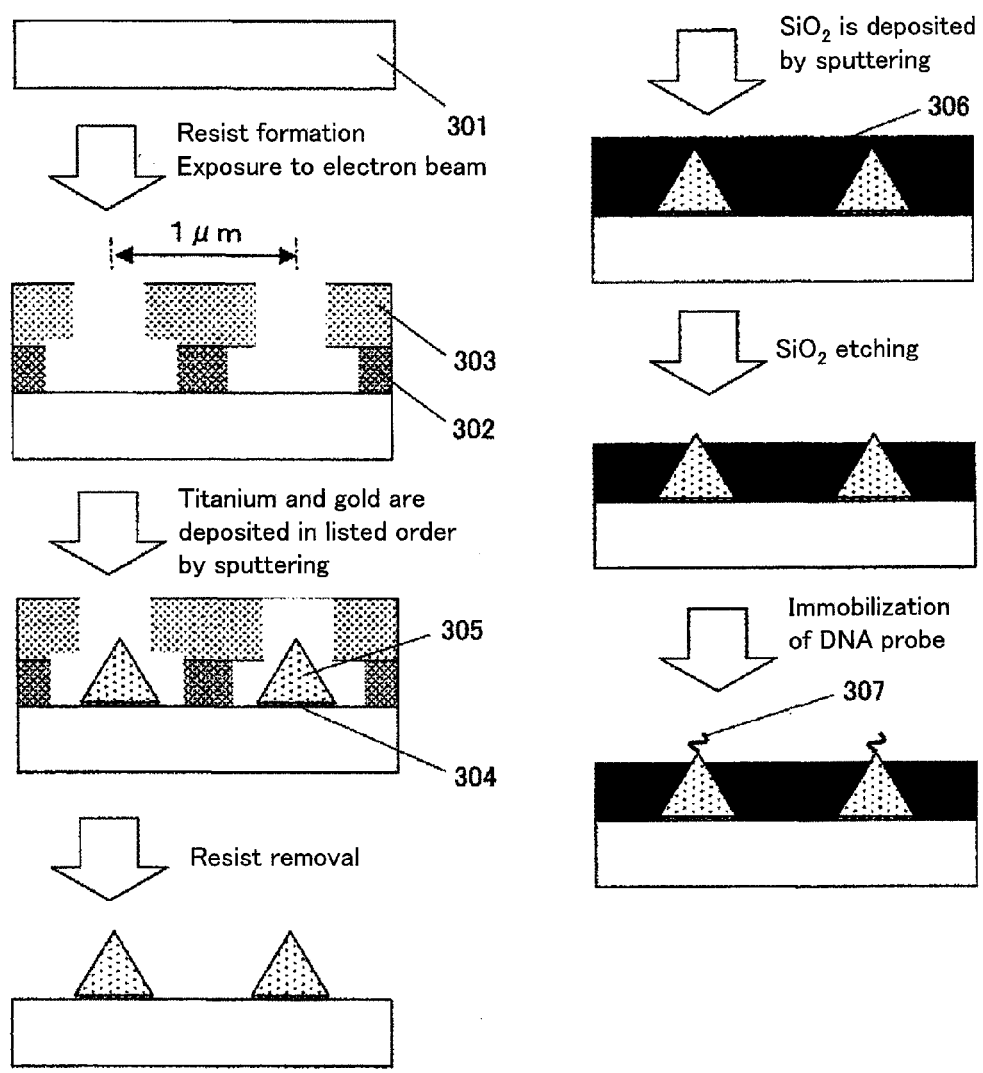
FIG. 3 is a view for explaining an example of the fabrication method for the nucleic acid analysis device of the present invention.

Description will now be given with reference to FIG. 3 with regard to a fabrication method for a nucleic acid analysis device having a structure having DNA probe immobilized on a conical end made of gold. A flat supporting substrate 301 is coated separately with two types of electron beam positive resists 302 and 303 by spin coating method. A glass substrate, a sapphire substrate, a resin substrate, or the like is used as the flat supporting substrate. For the device, a quartz substrate or a sapphire substrate having excellent light transmittance can be used if it is necessary to irradiate the device with excitation light from the rear surface opposed to the surface on which the metal structure is formed and the opposite rear surface. A combination of polymethyl methacrylate and a macromolecular resist having a structure capable of easy depolymerization by radical cutting, for example, can be used as the two types of electron beam positive resists. For the latter resist, it is preferable that the resist be capable of undergoing prebaking by a hot plate at 170° to 200° for about 2 to 5 minutes and also capable of undergoing electron beam writing at an electron dose of 20 µC/cm² to 50 µC/cm² at an accelerating voltage of 20 KV as a matter of practicality, and for example, the resists include ZEP-520A (available from Zeon Corporation). Alignment takes place using the position of a marker on the substrate and then, a direct electron beam exposure takes place twice, and thereby, a through hole is formed in each of the resists so that a hole diameter of the electron beam positive resist 302 closer to the substrate is larger than that of the electron beam positive resist 303. For example, the through holes having a diameter of 300 nm and a diameter of 100 nm, respectively, are formed. The through holes are used for a mask for deposition having a large taper. After the formation of the through holes, titanium 304 and gold 305 are deposited by sputtering according to the composition of the metal structure. Preferably, the titanium is used in order to reinforce a bond between the sapphire and the gold, or other metal such as chromium may be used. The gold sputtered film 305 has a conical shape as shown in FIG. 3. To control the conical shape, it is effective that the two resists each have different film thicknesses and hole diameters. After the removal of the two-layer resist, the $SiO_2$ film 306 is deposited by sputtering. Then, the $SiO_2$ film 306 is subjected to reactive ion etching (using $CF_4/O_2$) so that the tip end of the gold 305 is exposed. Then, by a hydroxysilane process, a hydroxyl group is introduced on the $SiO_2$ film 306 to thereby prevent non-singular adsorption. Finally, a DNA probe 307 whose end is modified with a thiol group is allowed to undergo a reaction, and thereby the nucleic acid analysis device having the structure having the DNA probe immobilized on the conical end made of gold can be brought into completion. It goes without saying that the above fabrication method may be used in the same manner even if silver or platinum, besides gold, is used.

Figure 4:
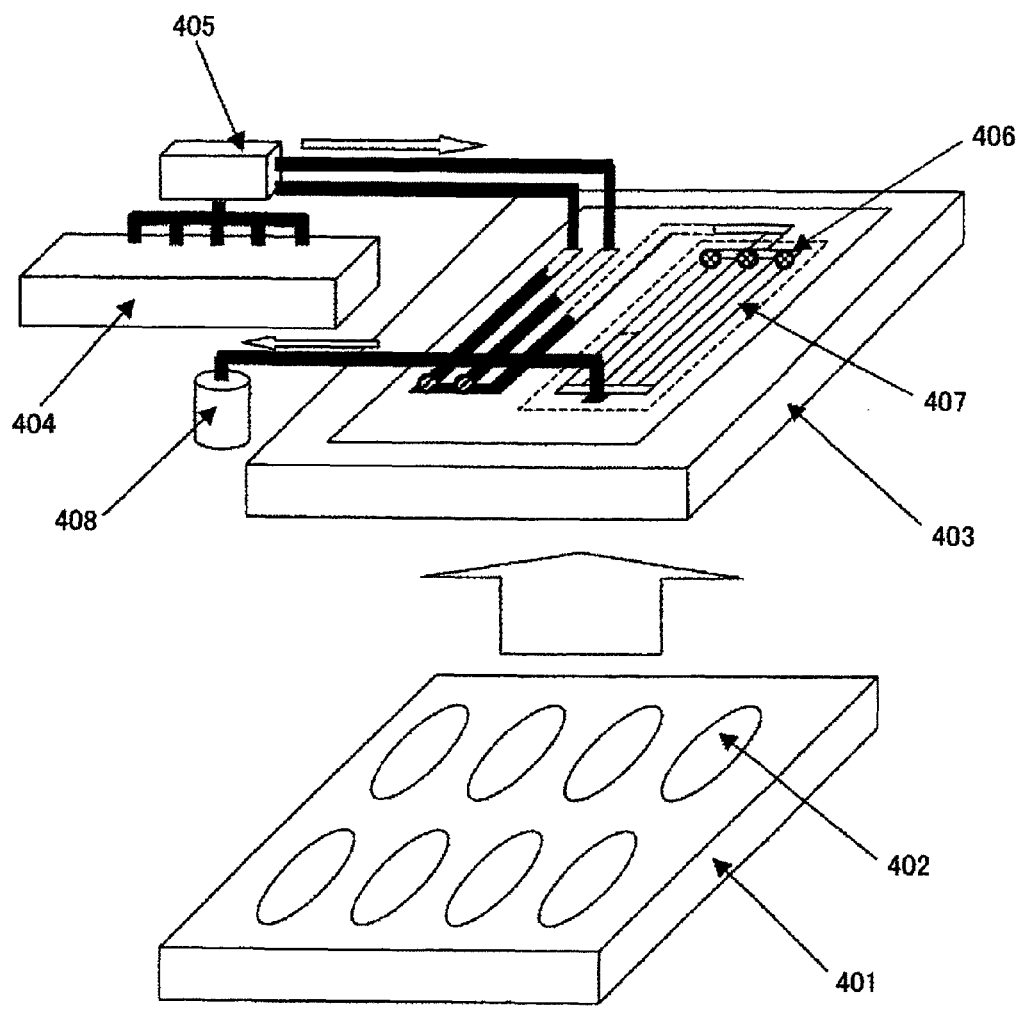
FIG. 4 is a view for explaining an example of the configuration of the nucleic acid analysis device of the present invention.

Description will be given with reference to FIG. 4 with regard to an example of a preferred configuration of the nucleic acid analysis device. Plural regions where metal structures are arranged in a lattice are mounted on a light-transmission supporting substrate 401. The metal structures are the two metal structures in proximity to each other between which the DNA probe is immobilized, or the metal structures having the structure having the DNA probe immobilized on the conical end made of gold, as previously mentioned. The pitch of arrangement can be appropriately set according to the nucleic acid sample to be analyzed, or specifications of the fluorescent detector. For example, if slide glass of 25 mm×75 mm is used as the light-transmission supporting substrate 401 and each of the regions where the metal structures are arranged in a lattice at intervals of 1 µm is 5 mm×8 mm, 40,000,000 types of nucleic acid molecules can be analyzed per region, and about 8 regions can be mounted on the light-transmission supporting substrate 401 (or the slide glass). Therefore, for example, if the device is used for RNA expression analysis, RNA of 400,000 molecules per cell is expressed, and thus, an analysis of the frequency of RNA expression can be done with sufficient accuracy as in the case of digital counting, so that about 8 analyses can be made on one substrate. As mentioned above, the mounting of plural regions on the light-transmission supporting substrate 401 can be accomplished by covering the light-transmission supporting substrate 401 with a reaction chamber 403 having a fluid channel preformed therein. The reaction chamber 403 is made of a resin base such as PDMS (Polydimethylsiloxane) having a fluid channel 407 preformed therein, and is fixedly attached onto the device for use. Specifically, the reaction chamber 403 includes: a temperature regulating unit 404 that preserves and performs temperature control on the nucleic acid sample, a reaction enzyme, a buffer, a nucleotide substrate, or the like; a dispensing unit 405 that feeds out a reaction solution; a valve 406 that controls the flow of the solution; and a waste fluid tank 408. As needed, the temperature regulating unit is provided for temperature control. At the completion of the reaction, a cleaning solution is fed through the fluid channel of the reaction chamber 403 and accommodated in the waste fluid tank 408.

Second Embodiment

Figure 5:
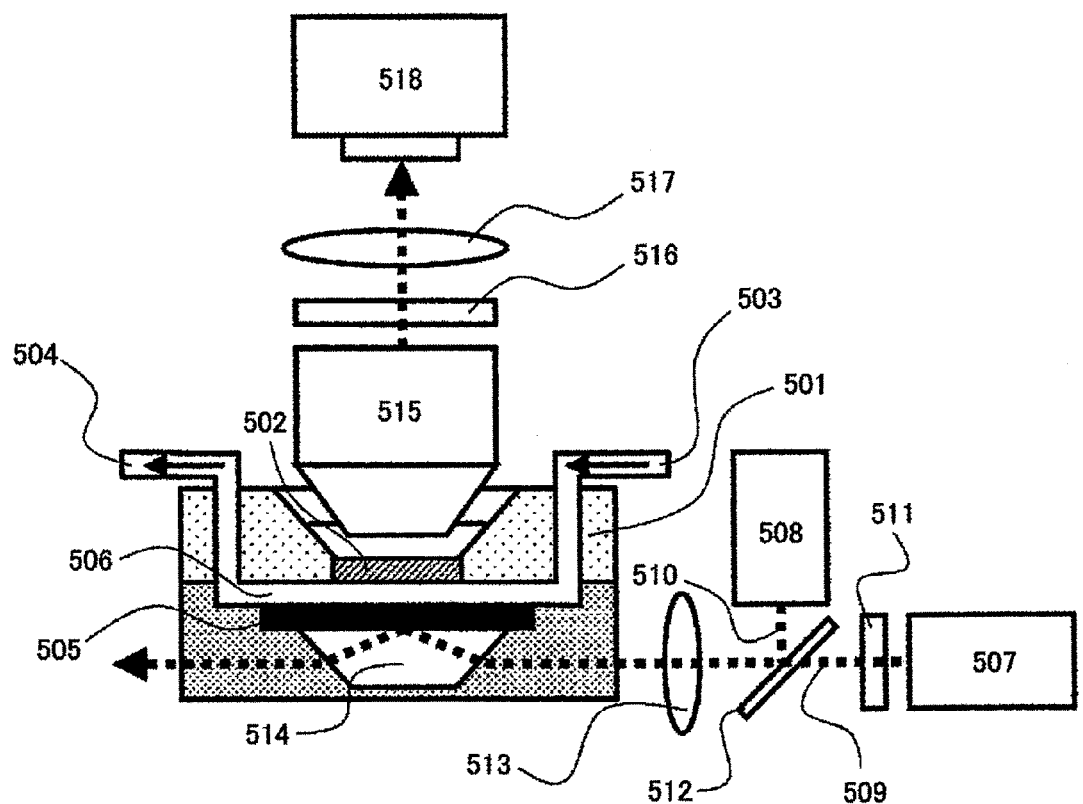
FIG. 5 is a view for explaining an example of a nucleic acid analyzer using the nucleic acid analysis device of the present invention.

Description will be given with regard to an embodiment of a nucleic acid analyzer. Description will be given with reference to FIG. 5 with regard to an example of a preferred configuration of the nucleic acid analyzer using the nucleic acid analysis device.

In the second embodiment, for the nucleic acid analysis device, there are provided a means for supplying nucleotide having fluorescent dye, a nucleic acid synthase, and the nucleic acid sample, a means for irradiating the nucleic acid analysis device with light, and a luminescence detecting means for making a measurement on fluorescence of the fluorescent dye captured in a nucleic acid chain due to a nucleic acid elongation reaction induced by the coexistence of the nucleotide, the nucleic acid synthase, and the nucleic acid sample on the nucleic acid analysis device. Specifically, the above-mentioned device 505 is installed in a reaction chamber composed of a cover plate 501, a detection window 502, and injection and discharge ports 503 and 504 that serve as solution change ports. Incidentally, PDMS (Polydimethylsiloxane) is used as a material for the cover plate 501 and the detection window 502. The thickness of the detection window 502 is set to 0.17 mm. Of laser light beams 510 and 509 from a YAG laser light source 507 (with a wavelength of 532 nm and an output of 20 mW) and a YAG laser light source 508 (with a wavelength of 355 nm and an output of 20 mW), only the light beam 509 is circularly polarized by a λ/4 plate 511, and the two laser light beams are coaxially adjusted by a dichroic mirror 512 (that reflects light of 410 nm or less) are then focused by the lens 513, and thereafter the device 505 is irradiated with the light through a prism 514 at a critical angle or more. According to the second embodiment, by laser irradiation, a localized surface plasmon is generated in the metal structure present on the surface of the device 505, and a phosphor of a target substance trapped by the DNA probe bonded to the metal structure is present in a fluorescence intensifying field. A phosphor is excited by laser light, and part of the intensified fluorescence exits through the detection window 502. Also, the fluorescence exiting through the detection window 502 is changed into parallel light beams through an objective lens 515 (X60, NA: 1.35, operating distance: 0.15 mm), background light and excitation light are cut off by an optical filter 516, and the light beams are focused through an imaging lens 517 onto a two-dimensional CCD camera 518 to form an image.

For a consecutive reaction method, the nucleotide containing a 3'-O-allyl group as a protecting group at position 3' OH of ribose and bonded to the fluorescent dye through an allyl group at position 5 of pyrimidine or at position 7 of purine can be used as the nucleotide with the fluorescent dye, as disclosed in P.N.A.S. 2006, vol. 103, pp 19635-19640. Since the allyl group is cut by light irradiation or by contact with palladium, quenching of the dye and control of the elongation reaction can be achieved at a time. Even for a consecutive reaction, it is not necessary to do cleaning for removal of unreacted nucleotide. Further, due to the unnecessity of the cleaning process, a measurement can be made on the elongation reaction in real time. In this case, the nucleotide does not have to contain the 3'-O-allyl group as the protecting group at position 3' OH of ribose, and the nucleotide bonded to the dye through a functional group capable of being cut by light irradiation can be used.

As described above, the use of the nucleic acid analysis device according to the second embodiment for fabrication of the nucleic acid analyzer eliminates a need for the cleaning process, thus achieves a reduction in analysis time and simplification of the device and the analyzer, enables not only consecutive reaction method but also real-time measurement of the base elongation reaction, and thus achieves a great improvement in throughput as compared to the prior art.

Third Embodiment

In general, the maximum size of the fluorescence intensifying effect of the localized surface plasmon is substantially equivalent to the diameter of the structure, and is specifically equal to 20 nm. On the other hand, the size of the nucleic acid is 34 nm for 10 bases, and the nucleic acid corresponding to an intensifying field of 20 nm is equivalent to 58.8 bases ($20 \div 3.4 \times 10 \approx 58.8$). Therefore, the device according to the first embodiment has difficulty in nucleotide sequence determination for the nucleic acid longer than 58 bases, unless there is provided a contrivance such as rounding the elongated nucleic acid or widening the fluorescence intensifying field. If the read base length is short, the reference rate of obtained sequence information with database is low.

Therefore, in the third embodiment, a nucleic acid synthase for the analysis of the nucleic acid in the sample is disposed in the region of generation of a localized surface plasmon, as distinct from the first and second embodiments. This enables the immobilization of the nucleic acid synthase in the region on which the fluorescence intensifying effect is exerted, and thus enables reading of a longer base length. Description will be given below, centering on differences from the first and second embodiments.

Figure 6:
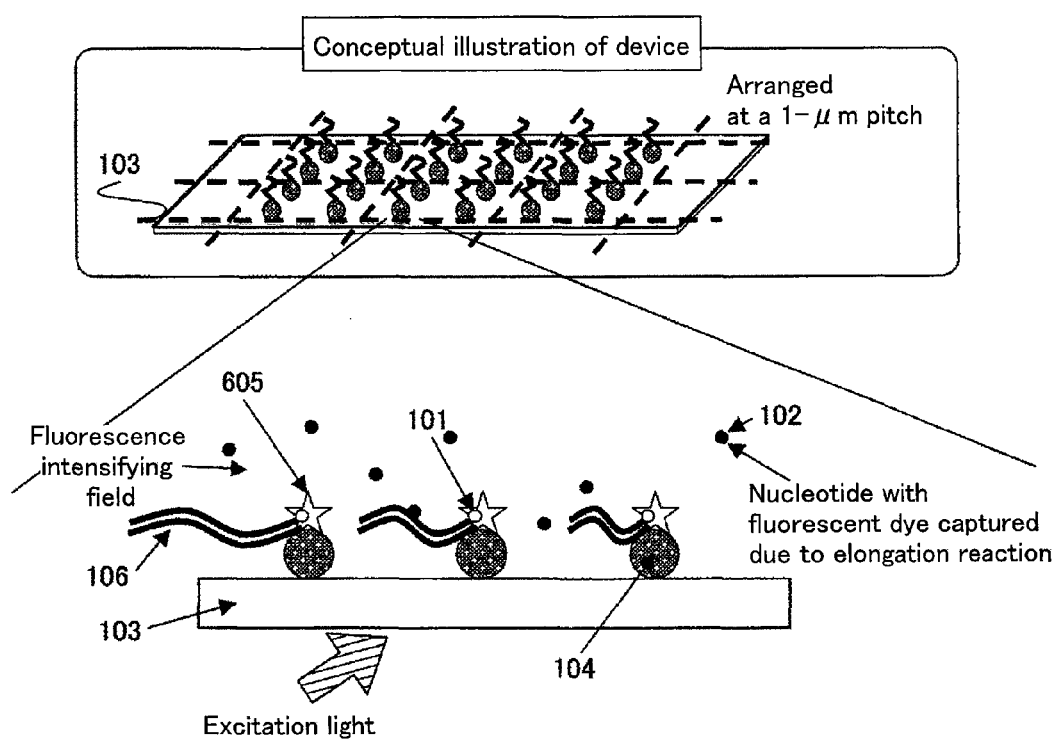
FIG. 6 is an illustration for explaining the concept of the nucleic acid analysis device of the present invention.

The concept of the device according to the third embodiment will be described with reference to FIG. 6. In order to distinguish between the fluorescent dye 101 trapped on a nucleic acid synthase 605 and the fluorescent molecule 102 of the unreacted substrate, it is required that a radiation process of only the dye 101 on the nucleic acid synthase occur efficiently. The influence of the fluorescence intensifying effect of the localized surface plasmon is exerted within a range of about 10 nm to 20 nm, and thus, when the localized surface plasmon is generated on the surface of a metal structure having the nucleic acid synthase 605 immobilized thereon, only the dye captured in the nucleic acid synthase 605 benefits from fluorescence intensification, so that a difference in fluorescence intensity arises between the captured dye and the suspended dye, or equivalently, the fluorescence intensity of the captured dye is several times to several tens of times or more times that of the suspended dye. The third embodiment is intended to find out a method for simple and easy immobilization of the nucleic acid synthase 605 in the region in which the localized surface plasmon is generated, and is also intended to provide a method capable of the fabrication of the regions on the order of tens of thousands to hundreds of thousands on the flat substrate 103. In the regions, the localized surface plasmon is generated as mentioned above.

In the third embodiment, an insulating layer is sandwiched in between the metal structures, the distance between the metal structures is controlled by controlling the thickness of the insulating layer, and the nucleic acid synthase is immobilized on the insulating layer.

An inorganic material such as $SiO_2$ or an organic material represented by polyimide can be used for the insulating layer to be interposed between the metal structures. In any of these instances, the fabrication of the desired metal structure with the nucleic acid synthase can be accomplished, using a difference in chemical properties between the surface of the insulating layer and the surface of the metal, by selecting an appropriate functional group, and either imparting the functional group to the insulating layer or allowing a functional group present in the nucleic acid synthase or a new functional group introduced into the nucleic acid synthase to react with the metal structure.

Also, the metal structure may be configured so that the structure has a sharp tip, the metal structure is coated with different metal from the above-mentioned metal in order that only the tip is exposed, and the difference in adhesion to the nucleic acid synthase between the above-mentioned metal and a material that coats it is utilized for immobilization of the nucleic acid synthase only on the tip of the metal.

For immobilization of the nucleic acid synthase on the exposed portion, a difference in chemical properties between the surface of the metal structure and the surface of the thin film can be utilized. For example, if gold is used as the metal and $SiO_2$ is used for the film that coats the metal, the nucleic acid synthase is immobilized only on the gold exposed portion by allowing the functional group present in the nucleic acid synthase or the new functional group introduced into the nucleic acid synthase to react with the functional group introduced on the surface of the gold. The appropriate size of the metal structure varies according to the wavelength of light for irradiation. In other words, a resonance frequency suitable for surface plasmon generation depends on the interaction between a group of free electrons and light on the surface of the metal structure. If visible light is used as excitation light, it is appropriate that the dimensions of the metal structure are such that both the width and height thereof lie between about 30 nm and 1000 nm; however, it is to be understood that the dimensions are not restricted to this condition. Also, the effect of the surface plasmon is equivalent even if the thin film that coats the metal structure is removed after the immobilization of the nucleic acid synthase on the tip by the above method. Preferably, the thin film that coats the metal structure is removed if the thin film adversely affects the properties of the nucleic acid analysis device.

The nucleic acid synthase is not particularly limited, provided that it is capable of elongation of the nucleic acid. Such nucleic acid synthases include various DNA polymerases if the nucleic acid is DNA. On the other hand, such nucleic acid synthases include various RNA polymerases if the nucleic acid is RNA.

Since a fabrication method for the nucleic acid analysis device having the nucleic acid synthase immobilized between the two metal structures in proximity to each other is equivalent to the first embodiment up to the immobilization of the nucleic acid synthase on the $SiO_2$ film, description thereof will be omitted. Although various methods for immobilization of the nucleic acid synthase on the $SiO_2$ film 207 can possibly be used, a method using an aminosilane process will be described as an example. In the aminosilane process, an amino group is introduced into the $SiO_2$ film 207. After that, N-(4-Maleimidobutyryloxy) succinimide (e.g., GMBS commercially available from Dojindo Laboratories) that is a bivalent reagent is allowed to undergo a reaction, and thereafter the nucleic acid synthase is allowed to undergo a reaction. By this process, the nucleic acid analysis device having the nucleic acid synthase immobilized between the two metal structures in proximity to each other can be brought into completion. As for the method for immobilization of the nucleic acid synthase, the above method is only illustrative, and a method utilizing physical adsorption to nitrocellulose, polyacrylamide, or the like, a method utilizing a specific affinity between histidine and nickel ion or cobalt ion, a method utilizing a biotin-avidin bond, or the like may be used. Furthermore, the metal structure can be fabricated in the same manner even if silver or platinum is used for the metal structure.

Since a fabrication method for a nucleic acid analysis device having a structure having the nucleic acid synthase immobilized on a conical end made of gold is equivalent to the first embodiment up to the immobilization of the nucleic acid synthase on the conical end of the gold, description thereof will be omitted.

As in the case of the first embodiment, the $SiO_2$ film 306 is subjected to reactive ion etching (using $CF_4/O_2$) so that the tip end of the gold 305 is exposed. Then, by a hydroxysilane process, a hydroxyl group is introduced on the $SiO_2$ film 306 to thereby prevent non-singular adsorption. Then, a SAM (Self-Assembled Monolayer) is formed by use of amino alkane thiol, an amino group is introduced on the surface of the gold, and thereafter a functional group that can be allowed to react with a thiol group is introduced by use of N-(4-Maleimidobutyryloxy) succinimide (e.g., GMBS commercially available from Dojindo Laboratories). Finally, a thiol group present in the nucleic acid synthase 307 undergoes a reaction with the functional group, and thereby the nucleic acid analysis device having the structure having the nucleic acid synthase immobilized on the conical end made of gold can be brought into completion. As for the method for immobilization of the nucleic acid synthase, the above method is only illustrative, and a method utilizing physical adsorption to nitrocellulose, polyacrylamide, or the like, a method utilizing a specific affinity between histidine and nickel ion or cobalt ion, a method utilizing a biotin-avidin bond, or the like may be used. Furthermore, the metal structure can be fabricated in the same manner even if silver or platinum is used for the metal structure.

Additionally, analysis by the nucleic acid analysis device described with reference to the third embodiment can also be performed by the nucleic acid analyzer equivalent to the second embodiment. Since the third embodiment is different from the second embodiment only in that the nucleic acid synthase is replaced by a primer, description thereof will be omitted. Furthermore, in this instance, the analyzer includes a means for supplying nucleotide having fluorescent dye, a primer and a nucleic acid sample to the nucleic acid analysis device; a means for irradiating the nucleic acid analysis device with light; and a luminescence detecting means for making a measurement on fluorescence of the fluorescent dye captured in a nucleic acid chain due to a nucleic acid elongation reaction induced by the coexistence of the nucleotide, the primer and the nucleic acid sample on the nucleic acid analysis device.

The embodiments may be appropriately used in combination.

What is claimed is:

1. A nucleic acid analysis device for analysis of nucleic acid in a sample through fluorometry, comprising:
    a substrate comprising a plurality of metal structures disposed thereon, wherein each of the plurality of metal structures (a) forms a projection above the substrate (b) has a base attached to the substrate and an apex extending above the substrate and (c) consists of one or more metals in which a localized surface plasmon is generated by light irradiation;
    an insulting layer, wherein the insulating layer is disposed above the substrate and around the plurality of metal structures in a manner that the apex of said each of the plurality of metal structures is exposed and not covered by the insulating layer;
    a nucleic acid synthase immobilized on the exposed surface of said each of the plurality of metal structures; and
    a nucleic acid probe bound to the nucleic acid synthase for the analysis of the nucleic acid in the sample, wherein one molecule of the nucleic acid probe is bound to each nucleic acid synthase, and the nucleic acid synthase is disposed in a region on which the localized surface plasmon is generated.

2. The nucleic acid analysis device according to claim 1, wherein said each of the plurality of metal structures has a conical shape.

3. The nucleic acid analysis device according to claim 1, wherein said of the plurality of metal structures is a polyhedron.

4. The nucleic acid analysis device according to claim 1, wherein said each of the plurality of metal structures consists of one or more noble metals selected from the group consisting of gold, silver and platinum.

5. The nucleic acid analysis device according to claim 1, wherein the plurality of metal structures are arranged in an array on the substrate.

6. The nucleic acid analysis device according to claim 1, further comprising:
    a means for supplying nucleotide having fluorescent dye, a nucleic acid synthase and a nucleic acid sample to the nucleic acid analysis device;
    a means for irradiating the nucleic acid analysis device with light; and
    a luminescence detector for making a measurement on fluorescence of the fluorescent dye captured in a nucleic acid chain due to a complementary sequence building reaction induced by the coexistence of the nucleotide, the nucleic acid synthase and the nucleic acid sample on the nucleic acid analysis device,
    wherein nucleotide sequence information on the nucleic acid sample is obtained.

7. The nucleic acid analysis device according to claim 1, further comprising:
    a dispensing unit for supplying nucleotide having fluorescent dye, a nucleic acid synthase and a nucleic acid sample to the nucleic acid analysis device;
    a light source for irradiating the nucleic acid analysis device with light; and
    a camera for making a measurement on fluorescence of the fluorescent dye captured in a nucleic acid chain due to a complementary sequence building reaction induced by the coexistence of the nucleotide, the nucleic acid synthase and the nucleic acid sample on the nucleic acid analysis device,
    wherein nucleotide sequence information on the nucleic acid sample is obtained.

* * * * *